(12) United States Patent
Jansen et al.

(10) Patent No.: US 8,692,003 B2
(45) Date of Patent: Apr. 8, 2014

(54) INCREASING THE IN VIVO BIOLOGICAL ACTIVITY OF BIOLOGICALLY ACTIVE COMPOUNDS

(75) Inventors: Frans Herwig Jansen, Oub-Turnhout (BE); Shahid Ahmed Soomro, Aachen (DE)

(73) Assignee: Dafra Pharma N.V., Turnhout (BE)

( * ) Notice: Subject to any disclaimer, the term of this patent is extended or adjusted under 35 U.S.C. 154(b) by 67 days.

(21) Appl. No.: 12/677,186

(22) PCT Filed: Sep. 10, 2008

(86) PCT No.: PCT/EP2008/007556
§ 371 (c)(1),
(2), (4) Date: Jun. 2, 2010

(87) PCT Pub. No.: WO2009/033706
PCT Pub. Date: Mar. 19, 2009

(65) Prior Publication Data
US 2010/0286393 A1    Nov. 11, 2010

(30) Foreign Application Priority Data
Sep. 10, 2007    (EP) .................... PCT/EP2007/007868

(51) Int. Cl.
*C07D 321/00*    (2006.01)

(52) U.S. Cl.
USPC ........................................................ 549/348

(58) Field of Classification Search
USPC ........................................................ 549/248
See application file for complete search history.

(56) References Cited

U.S. PATENT DOCUMENTS

| 6,156,790 | A  | 12/2000 | Posner et al. |
| 6,306,896 | B1 | 10/2001 | Scheiwe |
| 2005/0282804 | A1 | 12/2005 | Hölzer |

FOREIGN PATENT DOCUMENTS

| EP | 0362730 | * | 9/1989 | ........... C07D 493/20 |
| EP | 0362730 A1 | * | 9/1989 | |
| EP | 0362730 | * | 4/1990 | ........... C07D 493/20 |
| EP | 0362730 A1 | | 4/1990 | |
| EP | 1604992 A1 | | 12/2005 | |
| WO | 9922727 A1 | | 5/1999 | |
| WO | 03022855 A1 | | 3/2003 | |

OTHER PUBLICATIONS

Li et al. STN Accession No. 1982:492245, Document No. 97:92245, Abstract of Yaoxue Xuebao (1981), 16(6), 429-39.*
Zhang et al. STN Accession No. 1985:58925 Document No. 103:189255 Abstract OF Yiyao Gongye (1985), 16(6), 254-7.*
Rouchi, Chemical and Engineering News, 2003, 81 (41), 104-107.*
Dorwald F. A. Side Reactions in Organic Synthesis, 2005, Wiley: VCH, Weinheim p. IX of Preface p. 1-15.*
Venugoplan et al. Eur J &fed Chem (1995) 30,697-706.*
Li et al. Bioorganic & Medicinal Chemistry Letters, 1995, 5(16), 1791-1794.*
Jung et al. J. Med. Chem. 1990,33, 1516-1518.*
Nowak et al., "Synthesis of (+)-Artemisinin and (+)-Deoxoartemisinin from Arteannuin B and Arteannuic Acid", Tetrahedron,1998, pp. 319-336, vol. 54, No. 3-4, Elsevier Science Ltd., Amsterdam.
Parshikov et al., "Hydroxylation of 10-deoxoartenisinin to 15-hydroxy-10-deoxoartemisinin by *Aspergillus niger*", Biotechnology Letters, 2004, pp. 607-610, vol. 26. Netherlands.

* cited by examiner

*Primary Examiner* — Nizal Chandrakumar
(74) *Attorney, Agent, or Firm* — The Webb Law Firm

(57) ABSTRACT

The present invention relates to compounds with an increased in vivo biological activity, and especially an increased pharmaceutical activity, such as an anti-nematodal or antifungal activity, an immunosuppresive activity, a metabolism influencing activity and/or an anti-cancer activity. Specifically, the present invention relates to compound comprising an artemisinin derivative according to the general formula (I)

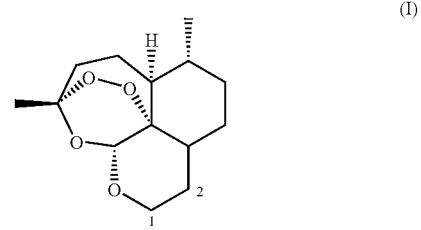

(I)

covalently linked at the 1 or the 2 position to a compound with a biological activity thereby increasing the biological activity of said compound or a pharmaceutically acceptable salt thereof.

1 Claim, No Drawings

INCREASING THE IN VIVO BIOLOGICAL ACTIVITY OF BIOLOGICALLY ACTIVE COMPOUNDS

DESCRIPTION

The present invention relates to compounds with an increased in vivo biological activity, and especially an increased pharmaceutical activity, such as an anti-nematodal or antifungal activity, an immunosuppresive activity, a metabolism influencing activity and/or an anti-cancer activity. The present invention further relates to a method for preparing said compounds and the use of said compounds for the treatment of mammals, preferably humans, in need of treatment.

The in vivo biological activity of a compound, and especially the pharmaceutical activity of a compound or a drug, is determined, amongst others, by its pharmacokinetic parameters.

In general, pharmacokinetic parameters are used to describe the response of the human or animal body to a drug. Examples of such parameters are absorption of the drug by, distribution of the drug through, and metabolic conversion or degradation of the drug in the human or animal body.

Further, pharmacodynamic parameters are used to describe the response of the human or animal body to a drug. In other words, pharmacodynamic parameters relate to the mechanism of activity of a compound or drug such as a receptor agonistic or antagonistic activity, membrane disruption, suppression or activation of an immune response, DNA-binding, influencing chemical reactions, influencing signaling cascades, etc.

Coupling, such as covalently coupling or linking, other compounds to a known drug can greatly influence its pharmacokinetic parameters such as its absorption by, its distribution through and/or its metabolic conversion or degradation by the human or animal body.

For example, by increasing the absorption of a drug through the (covalently) coupled compound, lower concentrations of a drug could be required to obtain a therapeutic effect compared to the required concentration of the drug not (covalently) coupled to the compound.

Similar effect are obtained when such (covalently) coupled compound beneficially improves the distribution of a drug, such as targeting it to specific locations in the body where it only locally exerts its therapeutic activity. An addition benefit could also be a reduced toxicity.

Also, lowering the concentration of the drug to be administered or chancing the treatment regime could be provided in case the (covalently) coupled compounds decrease or increase the metabolic conversion of the drug depending on the pharmaceutically active form of the drug.

It is also possible that the (covalently) coupled compound influences one or more pharmacodynamic parameters of a drug. In this case the effect could be additional, i.e., the sum of the pharmaceutical activity of the (covalently) coupled compound and the drug, or synergistic.

Further, it is possible that the (covalently) coupled compound in combination with the drug provides a not previous recognized or known beneficial pharmaceutical activity.

Regardless of the mechanism of action, i.e., improving, or even providing, pharmacokinetic and/or pharmacodynamic parameters or properties, of the (covalently) coupled compound, an improved and beneficial therapeutic effect can be obtained through, for example, a reduction of the amount the drug to be administered.

As another example, an improved beneficial therapeutic effect can be obtained because of the possibility to increase the concentration of the drug due to a decreased toxicity provided by, for example, an improved (local) distribution or an increased or decreased metabolic conversion.

Considering, amongst others, the above possible benefits and advantages of (covalently) coupling a compound to a known drug with respect to its pharmacokinetic and/or pharmacodynamic properties or characteristics, it a an object of the present invention to provide such combination of a (known) drug (covalently) coupled to a compound.

According to the present invention, this object, amongst others, is met by a compound comprising an artemisinin derivative according to the general formula (I):

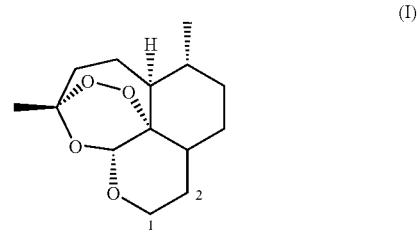

(I)

covalently linked at the 1 or the 2 position to a compound with a biological activity, preferably a pharmaceutical activity, thereby increasing the biological activity, preferably the pharmaceutical activity, of said compound.

It has surprisingly been found by the present inventors that covalently coupling an artemisinin derivative according to the general formula (I) to a compound with biological activity, preferably a drug, beneficially influences the biological activity, preferably the pharmaceutical activity, of said compound.

In most cases and preferably, the beneficial biological activity, preferably the pharmaceutical activity, is provided by advantageously influencing one or more pharmacokinetic parameters of a biologically active compound, preferably a drug, such as its absorption by, its distribution through and/or its metabolic conversion by the human or animal body.

The above however does not exclude that the covalently coupled artemisinin derivative according to the present invention, possibly additionally, influences the biological activity, preferably the pharmaceutical activity, of said biologically active compound by providing one or more improved, or even novel, pharmacodynamic properties.

The artemisinin derivative according to the general formula (I) comprises as starting compound at the 1 and/or 2 position at least one coupling group for reacting with the biologically active compound such as an —OH group.

Besides being provided with at least one coupling group at the 1 or 2 position, the artemisinin derivative starting compound according to the present invention can be further substituted at the 1 and/or 2 position with a $C_1$ to $C_6$ alkyl or aryl group, branched or unbranched, such as a methyl, ethyl or propyl group, preferably a methyl group.

One of the artemisinin derivatives according the general formula (I) of the present invention can be derived from a known intermediate of the biosynthesis of the antimalarial drug artemisinin, i.e., dihydroartemisinin (DHA).

According to this aspect of the present invention, also propionate, isopropyl ester, butyrate and acetate moieties on the 1 or 2 position of dihydroartemisinin (DHA) are especially suitable to be used according to the present invention.

In case of dihydroartemisinin, the 1 position of the initial artemisinin derivative comprises an —OH group allowing covalently coupling of a biologically active compound to the 1 position, for example, by an estrification reaction or an etherification reaction.

Such reactions are common general knowledge in the field of organic chemistry and can be found in most organic chemistry text books such as, for example, Organic Chemistry, John McMurry, Brooks/Cole, 6$^{th}$ edition.

Another starting artemisinin derivative providing formula (I) is deoxoartemisinin. In this starting compound, a possible coupling group, such as —OH, is provided at the 2 position.

Another starting artemisinin derivative providing formula (I) is anhydrodihydroartemisinin (AHA). This compound comprises a double bond between the 1 and 2 position allowing, through an intermediate reaction, covalently coupling of a biologically active compound to the 1 position or the 2 position, for example, by a nucleophile reaction of O, N or S to provide the corresponding derivatives at the 1 position, or a hydroxylation reaction by an anti-markofnikoff addition at position 2.

Such reactions are common general knowledge in the field of organic chemistry and can be found in most organic chemistry text books such as, for example, Organic Chemistry, John McMurry, Brooks/Cole, 6$^{th}$ edition.

Accordingly, in a preferred embodiment of the present invention the artemisinin derivative according to the present invention is derived from a compound chosen from the group consisting of dihydroartemisinin, anhydrodihydroartemisinin and deoxartemisinin In a preferred embodiment of the present invention, the biologically, preferably pharmaceutically, active compound, is coupled to the artemisinin derivative according to the present invention, such as anhydrodihydroartemisinin, through a sulfide (—S—), ether (—O—), ester (—OCO—) or amine (—N—) linkage.

Particularly preferred in this embodiment of the present invention are sulfide (—S—) and ether (—O—) linkages.

According to one preferred embodiment, the compound with a biological activity of the present invention is covalently linked to the artemisinin derivative of the present invention at the 1 position of a compound according to the general formula (I).

According to yet another preferred embodiment, the compound with a biological activity of the present invention is covalently linked to the artemisinin derivative of the present invention at the 2 position of a compound according to the general formula (I).

In a particularly preferred embodiment of the present invention, the biologically active compound covalently coupled to the artemisinin derivative is methyl N-(1H-benzimidazol-2-yl)carbamate.

Methyl N-(1H-benzimidazol-2-yl)carbamate is an anti-nematodal agent, and particularly a fungicide, also known under a number of synonyms such as carbendazim, carbendazole, mecarzole, funaben, etc.

Covalently coupling methyl N-(1H-benzimidazol-2-yl)carbamate with an artemisinin derivative according to the present invention beneficially improves the anti-nematodal, and particularly, the fungicide activity of this drug.

According to a most preferred aspect of this embodiment of the present invention, the present invention provides a compound according to formula (II):

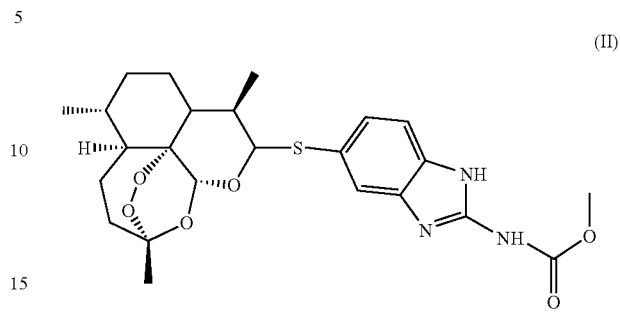

(II)

or a compound according to formula (III):

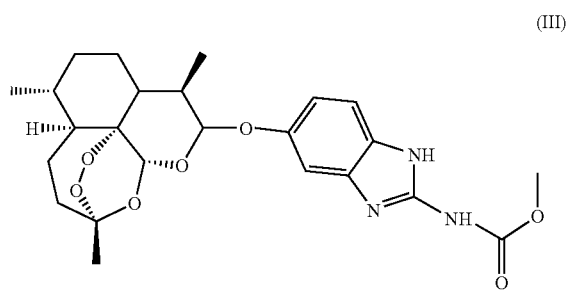

(III)

In another particularly preferred embodiment of the present invention, the biologically active compound covalently coupled to an artemisinin derivative according to the present invention is methoxyacetetic acid.

Methoxyacetetic acid is an immunosuppresive agent also known as methoxyethanoic acid or 2-methoxyacetetic acid.

Covalently coupling methoxyacetetic acid with an artemisinin derivative according to the present invention beneficially improves the immunosuppresive activity of this drug.

According to a most preferred aspect of this embodiment of the present invention, the present invention provides a compound according to formula (IV):

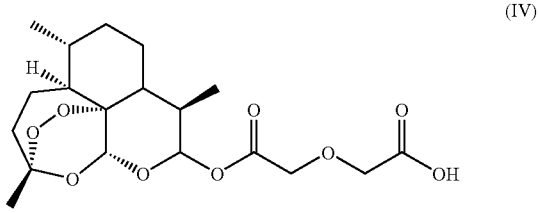

(IV)

In yet another particularly preferred embodiment of the present invention, the biologically active compound covalently coupled to an artemisinin derivative according to the present invention is 2,2-dichloroacetate.

2,2-dichloroacetate influences glucose metabolism, lowers lactate and activates the dehydrogenase complex.

Covalently coupling 2,2-dichloroacetate with a artemisinin derivative according to the present invention beneficially improves, amongst others, the metabolic influencing activity of this drug.

According to a most preferred aspect of this embodiment of the present invention, the present invention provides a compound according to formula (V):

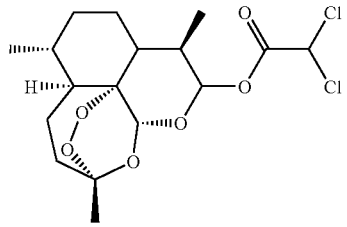

(V)

In still another particularly preferred embodiment of the present invention, the biologically active compound covalently coupled to the artemisinin derivative according to the present invention is 5-fluoro-1H-pyrimidine-2,4-dione.

5-fluoro-1H-pyrimidine-2,4-dione is an anti-neoplastic anti-metabolite. It interferes with DNA synthesis by blocking thymidylate synthase conversion of deoxyuridylic acid to thymidylic acid.

5-fluoro-1H-pyrimidine-2,4-dione is also known under the synonyms fluorouracil, fluoroplex, adrucil, efudex, timazin, etc.

Covalently coupling 5-fluoro-1H-pyrimidine-2,4-dione with an artemisinin derivative according to the present invention beneficially improves especially the anti-cancer activity of this drug.

According to a most preferred aspect of this embodiment of the present invention, the present invention provides a compound according to formula (VI):

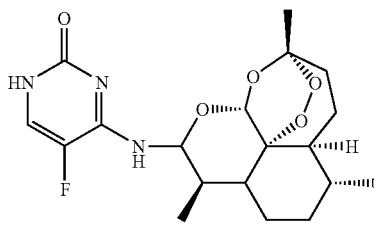

(VI)

In also a particularly preferred embodiment of the present invention, the biologically active compound covalently coupled to the artemisinin derivative according to the present invention is acetate.

Acetate is used, amongst others, internally as a counterirritant and also as a reagent.

Covalently coupling acetate with an artemisinin derivative according to the present invention beneficially improves especially the counterirritant activity of this drug.

According to a most preferred aspect of this embodiment of the present invention, the present invention provides a compound according to formula (VII):

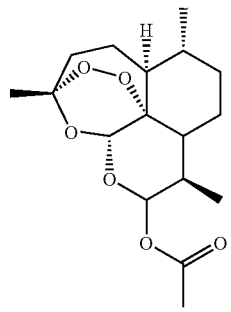

(VII)

In additional another particularly preferred embodiment of the present invention, the biologically active compound covalently coupled to the artemisinin derivative according to the present invention is iso-butyrate.

Iso-butyrate has, amongst others, an anti-proliferative effect. It is has an effect on acetylation and deacetylation of histones, thereby having an effect on cell growth control, differentiation and apoptosis.

Covalently coupling iso-butyrate with an artemisinin derivative according to the present invention beneficially improves especially the anti-proliferative activity of this drug.

According to a most preferred aspect of this embodiment of the present invention, the present invention provides a compound according to formula (VIII):

(VIII)

In still an additional particularly preferred embodiment of the present invention, the biologically active compound covalently coupled to an artemisinin derivative according to the present invention is butyrate.

Butyrate is, amongst others, a histamine antagonist

Covalently coupling butyrate with an artemisinin derivative according to the present invention beneficially improves especially the histamine antagonistic activity of this drug.

According to a most preferred aspect of this embodiment of the present invention, the present invention provides a compound according to formula (IX):

(IX)

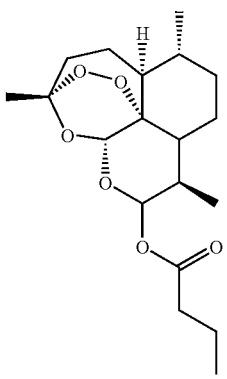

In yet another particularly preferred embodiment of the present invention, the biologically active compound covalently coupled to the artemisinin derivative according to the present invention is propylpentanoate.

Propylpentanoate is a fatty acid with anticonvulsant properties used in the treatment of epilepsy.

Propylpentanoate is also known under the synonyms valproic acid, epilim, convulex, eurekene, labazene, selenica, orfiril, valerin, etc.

Covalently coupling propylpentanoate with an artemisinin derivative according to the present invention beneficially improves especially the anticonvulsant activity of this drug.

According to a most preferred aspect of this embodiment of the present invention, the present invention provides a compound according to formula (X):

(X)

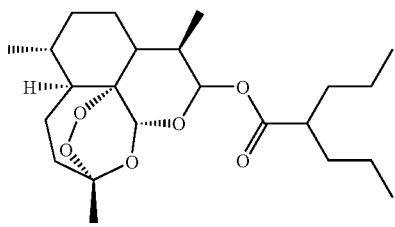

The present invention also relates to intermediate products of the compounds according to the present invention according to formula (XI):

(XI)

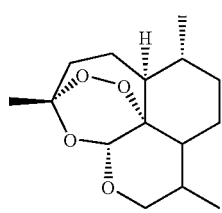

or according to the formula XII:

(XII)

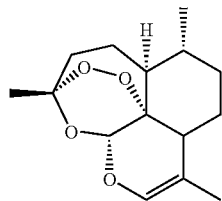

According to another aspect, the present invention relates to a method for obtaining a compound according to the present invention, wherein the method comprises covalently linking an artemisinin derivative as defined above with a compound with a biological activity as defined above through sulfide (—S—), ether (—O—), ester (—OCO—) or amine (—N—) linkage at the 1 or 2 position thereby increasing the biological activity of said biologically active compound.

Considering the therapeutic benefits provided by the compounds according to the present invention, the invention also relates to the use of an artemisinin derivative as defined above for increasing the biological activity of a compound as defined above.

According to another aspect, the present invention relates to a compound as defined above for use as a medicament.

According to yet another aspect, the present invention relates to the use of a compound as defined above for the preparation of a medicament for treating a mammal, preferably a human, in need of such treatment.

In a preferred embodiment of the above use, the present invention relates to the use of a compound as defined above for the preparation of a medicament for treating a mammal, preferably a human, suffering from a nematodal infection, wherein the compound having a biological activity is methyl N-(1H-benzimidazol-2-yl)carbamate.

In another preferred embodiment of the above use, the present invention relates to the use of a compound as defined above for the preparation of a medicament for treating a mammal, preferably a human, in need of immunosuppression wherein the compound having a biological activity is methoxyacetetic acid.

In yet another preferred embodiment of the above use, the present invention relates to the use of a compound as defined above for the preparation of a medicament for treating a mammal, preferably a human, suffering from a metabolic disease, wherein the compound having a biological activity is 2,2-dichloroacetate.

In still another preferred embodiment of the above use, the present invention relates to the use of a compound as defined above for the preparation of a medicament for treating a mammal, preferably a human, suffering from a metabolic disease, in need of immunosuppression or especially from cancer, wherein the compound having a biological activity is 5-fluoro-1H-pyrimidine-2,4-dione.

In an additional preferred embodiment of the above use, the present invention relates to the use of a compound as defined above for the preparation of a medicament for treating a mammal suffering from irritation, wherein the compound having a biological activity is acetate.

In another additional preferred embodiment of the above use, the present invention relates to the use of a compound as defined above for the preparation of a medicament for treating a mammal suffering from cancer, wherein the compound having a biological activity is iso-butyrate.

According to also an additional preferred embodiment of the above use, the present invention relates to the use of a compound as defined above for the preparation of a medicament for treating a mammal in need of immunosuppression, wherein the compound having a biological activity is butyrate.

The present invention will be further described using the following preparative examples of preferred embodiments of the present invention.

EXAMPLES

Example 1

General Synthesis of the Artemisinin Derivatives According to the Present Invention

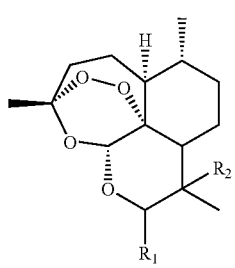

wherein $R_1$ and $R_2$ are H or a biologically active molecule according to the present invention under the provision that at least $R_1$ or $R_2$ is a biologically active molecule according to the present invention.

In a three neck flask containing 75 ml of liq. $NH_3$ was added approximately 0.1 g of Na in small pieces, then a methylbenzimidazole derivative 2.37 g (10 mmol) was slowly added and the mixture was set for stirring. The reaction was monitored by thin layer chromatography by taking small amounts out of reaction mixture.

After 2 h., the reaction was complete and subsequently quenched through the addition of ammonium chloride and the ammonia was allowed to evaporate.

Excess of Na was neutralized by the careful addition of water and the resulting product was repeatedly extracted with ether and recrystallized from dichloromethane/hexane yielding 1.8 g (8.07 mmol, 80.7%) of the desired product.

Example 2

Synthesis of Methyl 5-(dihydroartemisinyloxy)-1H-benzo[d]imidazol-2-ylcarbamate (1b)

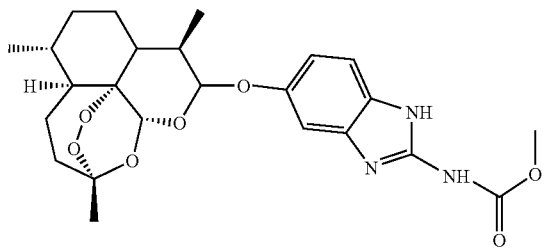

Boron trifluoride-diethyl ether (1 ml) was added to a stirred solution of dihydroartemisinin (DHA, 3.43 g, 12 mmol) and benzimidazole derivative (methyl N-(1H-benzimidazol-2-yl) carbamate, 1.94 g, 10 mmol) in dry diethyl ether (50 ml). The mixture was stirred at room temperature overnight and subsequently quenched with saturated aqueous $NaHCO_3$ and dried over $MgSO_4$. Filtration and concentration of the filtrate provided a residue which on chromatography with ethyl acetate/hexane (5:95-10:90) provided the product as a yellow solid.

The product obtained was further recrystallized from dichloromethane (mixture of epimers) as a yellow solid (2.98 g, 63%), m.p. 172-175° C.

1H NMR: 0.86-1.80 (m, 17 H), 1.99-2.02 (m, 1 H), 2.13-2.23 (m, 1H), 2.23-2.28 (m, 0.5H), 3.71 (s, 3H), 4.78 (s), 5.50 (m, 1H), (s), 5.41 (s, 1H), 5.56-5.58 (two singlets, 1H), 6.78-6.90 (m, 1H), 7.25-7.69 (m, 2H).

Example 3

Synthesis of 2-((Dihydroartemisinylcarbonyl)methoxy)acetic acid (2a)

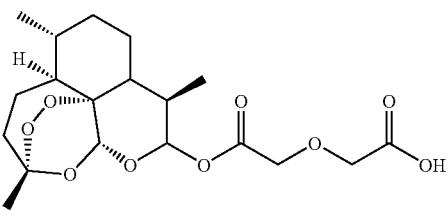

4-(Dimethylamino)pyridine (1.95 g, 16 mmol) and diglycolic anhydride (3.48 g, 30 mmol) were added to a stirred solution of DHA (2.84 g, 10 mmol) in dichloromethane (50 ml) and the reaction mixture was continuously stirred overnight.

The solvent was removed under reduced pressure and the residue was purified by column chromatography with ethyl acetate/hexane (10:90) to provide the product as a white solid (3.80 g, 95%). Recrystallization from ethyl acetate/hexane provided white needles (m.p. 168-171° C.)

1HNMR 0.86 (d, J=7.0 Hz, 3 H, 9-Me), 0.97 (d, J=5.95 Hz, 3 H, 6-Me), 1.45 (s, 3 H, 3-Me), 1.23-1.94 (m, 9 H), 2.04 (ddd, J=14.5, 5.0, 3.0 Hz, 1 H), 2.39 (ddd, J=14.5, 5.0, 3.0 Hz, 1 H), 2.55 (m, 1H, H-9), 4.25 (s, 2 H, OCH2COO), 5.40 (s, 2H, COCH2O) 5.45 (s, 1H, H-12), 5.850 (d, J=10.0 Hz, 1 H, H-10)

Example 4

Synthesis of Dihydroartemisinyl-2,2-dichloroacetate

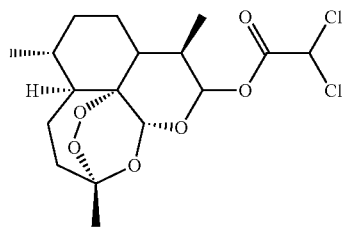

4-(Dimethylamino)pyridine (1.95 g, 16 mmol), diglycolic anhydride (3.48 g, 30 mmol) and DHA (2.84 g, 10 mmol) were used for the synthesis using the above method except that the eluent for chromatography was ethyl acetate/hexane (5:95). The product was obtained as yellow solid (3.44 g, 87%), m.p. 160-163° C.

1HNMR 0.86 (d, J=7.0 Hz, 3 H, 9-Me), 0.97 (d, J=5.95 Hz, 3 H, 6-Me), 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 3.0 Hz, 1 H), 2.55 (m, 1H, H-9), 5.40 (s, 1H, H-12), 5.90 (d, J=10.0 Hz, 1 H, H-10), 6.25 (s, 1 H, COCHCl2).

Example 5

Synthesis of 5-Fluoro-4-(dihydroartemisinyl amino)pyrimidin-2 (1H)-one

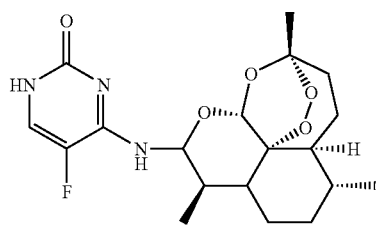

Boron trifluoride-diethyl ether (1 ml) was added to a stirred solution of DHA (2.56 g, 9 mmol) and F-uracil (1.04 g, 8.05 mmol) in dry diethyl ether (50 ml).

The mixture was stirred at room temperature overnight and subsequently quenched with saturated aqueous NaHCO₃ and dried over MgSO₄.

Filtration and concentration of the filtrate provided a residue which on chromatography with ethyl acetate/hexane (10: 90) provided the product as a yellow solid (mixture of epimers, 2.36 g, 74%), m.p. 165-170° C.

1HNMR 0.86 (d, J=7.0 Hz, 3 H, 9-Me), 0.97 (d, J=5.95 Hz, 3 H, 6-Me), 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 3.0 Hz, 1 H), 2.55 (m, 1H, H-9), 5.40 (s, 1H, H-12), 5.90 (d, J=10.0 Hz, 1 H, H-10),

Example 6

Synthesis of Anhydrodihydroartemisinin (AHA)

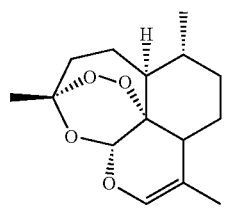

Boron trifluoride-diethyl ether (3 ml) was added to a stirred solution of DHA (2.56 g, 9 mmol) at 0° C. and the mixture was slowly brought to room temperature, stirred for 2 hours and subsequently quenched with saturated aqueous NaHCO₃ and dried over MgSO₄.

Filtration and concentration of the filtrate provided a residue which on chromatography with ethyl acetate/hexane (10: 90) provided the product as white solid (2.15 g, 90%), m.p. 95-98° C.

1HNMR 0.98 (d, J=5.8 Hz, 3 H, 6-Me), 1.02-1.39 (m, 2 H), 1.42 (m, 3 H, 9-Me), 1.44-1.75 (m, 8 H), 1.87-1.96 (m, 1 H), 2.00-2.12 (m, 2 H), 2.35-2.46 (m, 1 H), 5.54 (s, 1 H, H-12), 6.18 (s, J_1 H, 10-H) ppm.

Example 7

Synthesis of Deoxoartemisinin

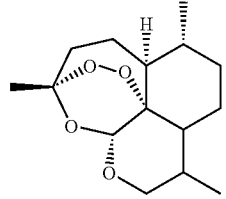

A solution of dihydroartemisinin (ADH, 456 mg, 1.6 mmol) in dry CH₂Cl₂ (16 ml) in a 50 ml round bottom flask under an argon atmosphere was cooled to −20° C.

To this solution were added triethylsilane (0.40 ml, 2.4 mmol) and boron trifluoride etherate (0.24 ml, 1.92 mmol). The solution was then allowed to warm to 5° C. over 2 h., and subsequently 15 ml of water was added.

The organic layer was separated, washed several times with water and dried over Na₂SO₄. The solution was concentrated and the crude product was purified by flash chromatography (hexane/CH₂Cl₂/6:4) to provide 380 mg pure product (88%), m.p. 104-106° C.

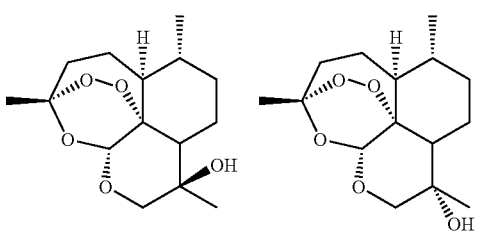

To a solution of anhydrodihydroartemisinin (AHA) (2.08 g, 7.8 mmol) in THF (20 ml), was dropwise added a solution of BH$_3$/THF complex in THF soln. (1 M; 14 ml) with ice-cooling. After being stirred at room temperature for 1 h, the mixture was treated with THF-water (1:1; 4 ml), followed by a mixture of aq. KOH (10%; 10 ml) and aq. H$_2$O$_2$ (50%; 4 ml).

Thereafter, the reaction mixture was stirred for 5 min, filtered and evaporated. The residue was washed with water and taken up into Et$_2$O and the ethereal solution was dried (MgSO$_4$) and evaporated to provide a white solid of a mixture of isomers which were separated by column chromatography (hexane/ethyl acetate).

Example 8

Synthesis of dihydroartemisinylacetate

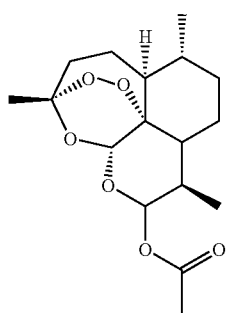

4-(Dimethylamino)pyridine (0.5 g, 4.1 mmol) and Acetic anhydride anhydride (3.06 g, 30 mmol) were added to a stirred solution of DHA (7.1 g, 25 mmol) in dichloromethane (400 ml) and the reaction mixture was continuously stirred overnight. The solvent was removed under reduced pressure and the residue was purified by column chromatography with ethyl acetate/hexane (10:90) to provide the product as a white solid (6.80 g, 84%). Recrystallization from ethyl acetate/hexane provided white needles (m.p. 129-131° C.)

1HNMR: 0.86 (d, J=7.0 Hz, 3 H, 9-Me), 0.97 (d, J=5.95 Hz, 3 H, 6-Me), 1.45 (s, 3 H, 3-Me), 1.23-1.94 (m, 9 H), 2.04 (ddd, J=14.5, 5.0, 3.0 Hz, 1H), 2.12 (s, 3 H, H—COCH3), 2.39 (ddd, J=14.5, 5.0, 15 3.0 Hz, 1 H), 2.55 (m, 1H, H-9), 5.45 (s, 1H, H-12), 5.850 (d, J=10.0 Hz, 1 H, H-10).

Example 9

Synthesis of dihydroartemisinyl iso-butyrate

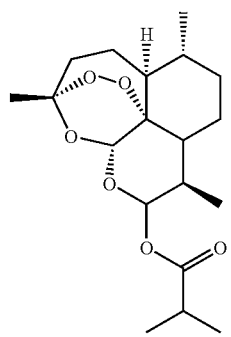

4-(Dimethylamino)pyridine (0.6 g, 4.9 mmol) and Isobutyric anhydride (4.0 g, 25 mmol) were added to a stirred solution of DHA (5 g, 17.6 mmol) in dichloromethane (200 ml) and the reaction mixture was continuously stirred overnight. The solvent was removed under reduced pressure and the residue was purified by column chromatography with ethyl acetate/hexane (10:90) to provide the product as a dense liquid (6.80 g, 84%).

1HNMR: 0.86 (d, J=7.0 Hz, 3 H, 9-Me), 0.97 (d, J=5.95 Hz, 3 H, 6-Me), 1.17-1.24 (m, 6 H) 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 15 3.0 Hz, 1 H), 2.55 (m, 1H, H-9), 2.68 (m, 1H, COCH), 5.45 (s, 1H, H-12), 5.850 (d, J=10.0 Hz, 1H, H-10).

Example 10

Synthesis of dihydroartemisinylbutyrate

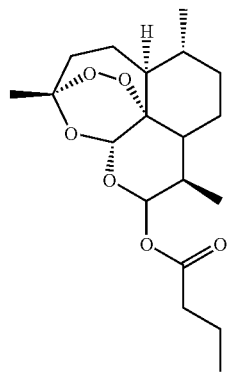

4-(Dimethylamino)pyridine (0.6 g, 4.9 mmol) and Isobutyric anhydride (4.0 g, 25 mmol) were added to a stirred solution of DHA (5 g, 17.6 mmol) in dichloromethane (300 ml) and the reaction mixture was continuously stirred overnight. The solvent was removed under reduced pressure and the residue was purified by column chromatography with ethyl acetate/hexane (10:90) to provide the product as a dense liquid (5.9 g, 95%).

1HNMR: 0.86 (d, J=7.0 Hz, 3 H, 9-Me), 0.97 (d, J=5.95 Hz, 3 H, 6-Me), 1.17-1.24 (m, 6 H), 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 15 3.0 Hz, 1 H), 2.55 (m, 1H, H-9), 2.68 (m, 1H, COCH), 5.45 (s, 1H, H-12), 5.850 (d, J=10.0 Hz, 1H, H-10).

Example 11

Synthesis of dihydroartemisinyl-2-propylpentanoate

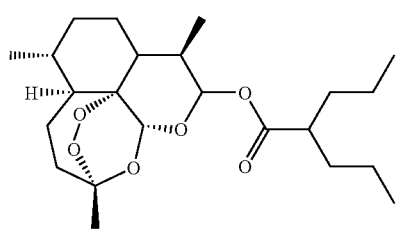

4-(Dimethylamino)pyridine (0.5 g, 4.1 mmol) and triethylamine (3.03 g, 30 mmol) were added to a stirred solution of DHA (7.1 g, 25 mmol) in dichloromethane (400 ml).

To this solution was added 2-Proplypentanlychlorid (4.87 g, 30 mmol) at −30° C., the reaction mixture was continuously stirred for 2 hours, slowly brought to room temperature and stirred overnight.

The solvent was removed under reduced pressure and the residue was purified by column chromatography with ethyl acetate/hexane (10:90) to provide the product as a white solid (10.22 g, 80%). Recrystallization from ethyl acetate/hexane provided white needles (m.p. 141-145° C.)

1HNMR: 0.86 (d, J=7.0 Hz, 3 H, 9-Me), 0.90 (t, 6H), 0.97 (d, J=5.95 Hz, 3 H, 6-Me), 1.33 (m, 4H), 1.45 (s, 3 H, 3-Me), 1.64 (m, 4H), 1.23-1.94 (m, 9 H), 2.04 (ddd, J=14.5, 5.0, 3.0 Hz, 1H), 2.29 (t, 1H), 2.39 (ddd, J=14.5, 5.0, 15 3.0 Hz, 1 H), 2.55 (m, 1H, H-9), 5.45 (s, 1H, H-12), 5.850 (d, J=10.0 Hz, 1 H, H-10).

Example 12

Synthesis of Dihydroartemisinyl 2,2-Dimethylpropianate

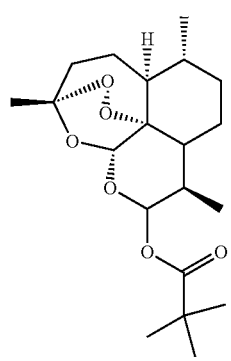

4-(Dimethylamino)pyridine (0.5 g, 4.1 mmol) and Trimethylacetic anhydride (5.59 g, 30 mmol) were added to a stirred solution of DHA (7.1 g, 25 mmol) in dichloromethane (400 ml) and the reaction mixture was continuously stirred overnight. The crude mixture was washed with water (2×100 ml) and solvent was removed under reduced pressure and the product was recrystallized from ethyl acetate/hexane providing a white solid which melts at 101-104° C. (6.9 g, 75%).

1HNMR: 0.86 (d, J=7.0 Hz, 3 H, 9-Me), 0.97 (d, J=5.95 Hz, 3 H, 6-Me), 1.25 (s, 9H C(CH)3), 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 15 3.0 Hz, 1 H), 2.55 (m, 1H, H-9), 5.45 (s, 1H, H-12), 5.850 (d, J=10.0 Hz, 1 H, H-10).

Example 13

Synthesis of Dihydroartemisinylthioethyl

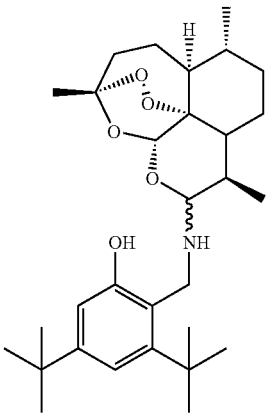

DHA (7.1 g, 25 mmol) and cystamine (2.7 g, 35 mmol) were dissolved in 300 ml dichloromethane and borontrifluoride-diethyl ether (10 ml) was slowly added at 0° C. The reaction mixture stirred for 3 hours at 0° C. and subsequently 1 hour at room temperature. The reaction was quenched with 5% NaHCO₃ and extracted with dichloromethane. The solvent was removed under reduced pressure and the residue was purified by column chromatography with ethyl acetate/hexane (10:90) to provide the product as a brown wax, yield 6.5 g.

1HNMR: 0.86 (d, J=7.0 Hz, 3 H, 9-Me), 0.97 (d, J=5.95 Hz, 3 H, 6-Me), 1.25, 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 15 3.0 Hz, 1 H), 2.55 (m, 1H, H-9), 2.9 (t, 2H), 3.1 (t, 2H), 4.56 (d, J=10.0 Hz, 1 H, H-10), 5.31 (s, 1H, H -12).

Example 14

Synthesis of 3,5-di-tert-butyl-2-(Dihydroartemisinylaminomethyl)phenol

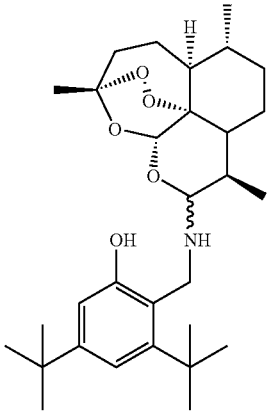

DHA (7.1 g, 25 mmol) and 3,5-di-tert-butyl-2-(aminomethyl)phenol (7.06 g, 30 mmol) were dissolved in 300 ml dichloromethane and borontrifluoride-diethyl ether (10 ml) was added slowly at 0° C. The reaction mixture was stirred for 3 hours at 0° C. and subsequently 1 hour at room temperature. The reaction was quenched with 5% NaHCO$_3$ and extracted with dichloromethane. The solvent was removed under reduced pressure and the residue was purified by column chromatography with ethyl acetate/hexane (20:80) to provide the product as a solid, yield 6.0 g.

1HNMR: 0.86 (d, J=7.0 Hz, 3 H, 9-Me), 0.97 (d, J=5.95 Hz, 3 H, 6-Me), 1.34 (s, 18H), 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 15 3.0 Hz, 1 H), 2.55 (m, 1H, H-9), 3.91 (s, 2H), 5.850 (d, J=10.0 Hz, 1 H, H-10), 5.45 (s, 1H, H-12), 6.44 (d, 1H), 6.76 (d, 1H).

Example 15

Synthesis of Dihydroartemisinyl N,N-Dimethylacetamide

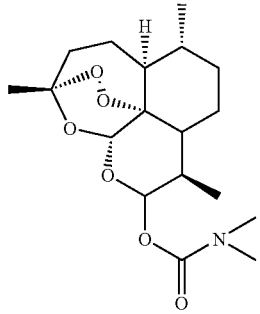

4-(Dimethylamino) pyridine (0.5 g, 4.1 mmol) and Dimethylcarbomoyl chloride (3.23 g, 30 mmol) were added to a stirred solution of DHA (7.1 g, 25 mmol) in dichloromethane (400 ml) and the reaction mixture was continuously stirred overnight. The crude was washed with water (2×100 ml) and solvent was removed under reduced pressure and the product was recrystallized from ethyl acetate/hexane provided yellow solid, yield 8.0 g (90%).

1HNMR: 0.86 (d, J=7.0 Hz, 3 H, 9-Me), 0.97 (d, J=5.95 Hz, 3 H, 6-Me), 1.45 (s, 3 H, 3-Me), 1.23-1.94 (m, 9 H), 2.04 (ddd, J=14.5, 5.0, 3.0 Hz, 1H), 2.39 (ddd, J=14.5, 5.0, 15 3.0 Hz, 1 H), 2.55 (m, 1H, H-9), 2.90 (s, 6H, N(CH$_3$)2 5.45 (s, 1H, H-12), 5.850 (d, J=10.0 Hz, 1 H, H-10).

The invention claimed is:
1. A composition comprising at least one of

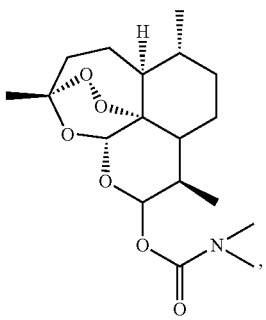

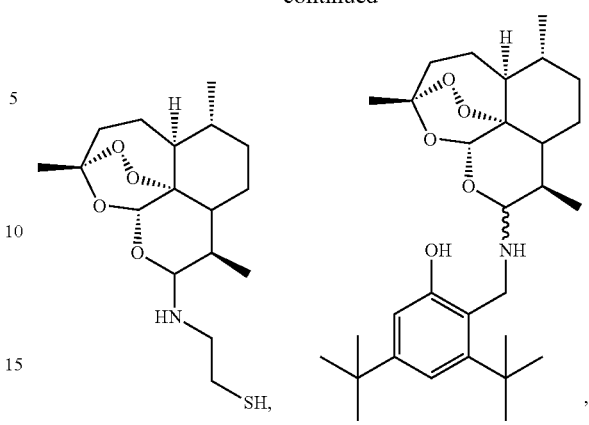

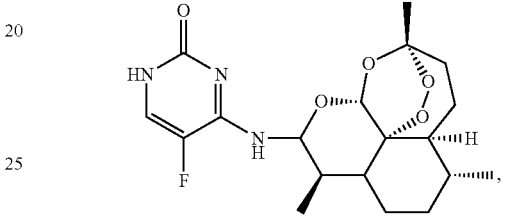

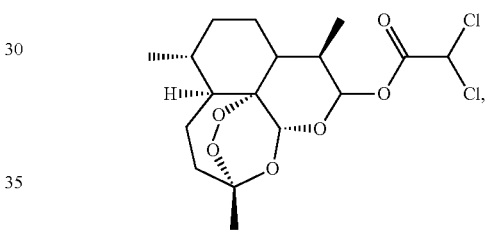

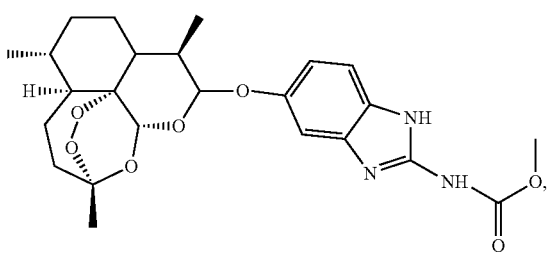

and

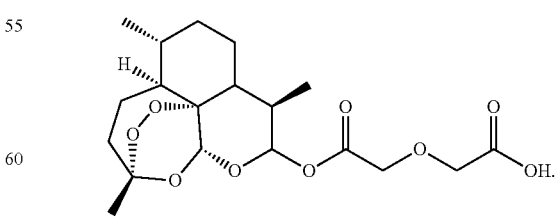

* * * * *

UNITED STATES PATENT AND TRADEMARK OFFICE
CERTIFICATE OF CORRECTION

PATENT NO. : 8,692,003 B2
APPLICATION NO. : 12/677186
DATED : April 8, 2014
INVENTOR(S) : Frans Herwig Jansen et al.

Page 1 of 1

It is certified that error appears in the above-identified patent and that said Letters Patent is hereby corrected as shown below:

On the Title Page, Item (75) Inventors, Page 1, Column 1, Line 1, delete "Oub-Turnhout" and insert
-- Oud-Turnhout --

Signed and Sealed this
Twelfth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,692,003 B2                                                                    Page 1 of 1
APPLICATION NO.   : 12/677186
DATED             : April 8, 2014
INVENTOR(S)       : Jansen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 275 days.

Signed and Sealed this
Twenty-ninth Day of September, 2015

Michelle K. Lee
*Director of the United States Patent and Trademark Office*